(12) United States Patent
Hürlimann et al.

(10) Patent No.: US 6,894,493 B2
(45) Date of Patent: May 17, 2005

(54) METHOD AND APPARATUS FOR NMR MEASUREMENT OF MAGNETIC MATERIALS

(75) Inventors: Martin D. Hürlimann, Ridgefield, CT (US); Abigail Matteson, Danbury, CT (US); Jermane Edward Massey, Houston, TX (US); David F. Allen, Brookfield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/730,797

(22) Filed: Dec. 9, 2003

(65) Prior Publication Data

US 2004/0164735 A1 Aug. 26, 2004

Related U.S. Application Data

(60) Provisional application No. 60/440,476, filed on Jan. 16, 2003.

(51) Int. Cl.$^7$ ............................................. G01V 3/00
(52) U.S. Cl. ........................................ 324/303; 324/300
(58) Field of Search ................................. 324/303, 300, 324/306, 307, 309

(56) References Cited

U.S. PATENT DOCUMENTS

| | | | |
|---|---|---|---|
| 3,484,680 A | 12/1969 | Hurlbert | 324/0.5 |
| 3,657,730 A | 4/1972 | Robinson et al. | 324/0.5 |
| 3,775,671 A | 11/1973 | Brown | 324/0.5 R |
| 5,023,551 A | 6/1991 | Kleinberg et al. | 324/303 |
| 5,055,787 A | 10/1991 | Kleinberg et al. | 324/303 |
| 5,055,788 A | 10/1991 | Kleinberg et al. | 324/303 |
| 5,153,514 A | 10/1992 | Griffin et al. | 324/303 |
| 5,796,252 A | 8/1998 | Kleinberg et al. | 324/303 |
| 6,462,542 B1 | 10/2002 | Venkataramanan et al. | 324/303 |
| 6,522,136 B1 | 2/2003 | Hurlimann et al. | 324/303 |
| 6,570,382 B1 * | 5/2003 | Hurlimann et al. | 324/303 |

FOREIGN PATENT DOCUMENTS

| | | |
|---|---|---|
| GB | 925630 | 5/1963 |
| GB | 1002540 | 8/1965 |

OTHER PUBLICATIONS

Bryar et al. Paramagnetic Effects of Iron(III) Species on Nuclear Magnetic Relaxation of Fluid Protons in Porous Media. *Journal of Magnetic Resonance* 142 (2000), pp. 74–85.

Hurlimann, M. D. et al. "Quantitative Measurement of Two–Dimensional Distribution Functions of Diffusion and Relaxation in Grossly Inhomogeneous Fields". *J. Mag. Reson.*, vol. 157, pp. 31–42 (2002).

Hurlimann, M. D. et al. "Diffusion–Editing: New NMR Measurement of Saturation and Pore Geometry", *SPWLA*, 43rd Annual Logging Symposium, Paper FFF, pp. 1–14 (Jun. 2002).

Hurlimann, M. D. et al. "The Diffusion–Spin Relaxation Time Distribution Function as an Experimental Probe to Characterize Fluid Mixtures in Porous Media". *J. Chem. Phys.*, vol. 117, No. 22, pp. 10223–10232 (Dec. 2002).

Hurlimann, M. D. et al. "Diffusion–Relaxation Distribution Functions of Sedimentary Rocks in Different Saturation States". *Elsevier, Magnetic Resonance Imaging*, vol. 21, pp. 305–310 (2003).

* cited by examiner

Primary Examiner—Brij B. Shrivastav
(74) Attorney, Agent, or Firm—Jody Lynn DeStefanis; William B. Batzer; Dale Gaudier

(57) ABSTRACT

The present invention relates to a method and apparatus for determining the presence of magnetic materials in a media, such as an earth formation. More specifically, the method of the present invention correlates a diffusion-relaxation calibration function representative of magnetic materials with a 2-D function developed using diffusion-editing to determine the presence and relative content of magnetic materials in a media.

29 Claims, 13 Drawing Sheets

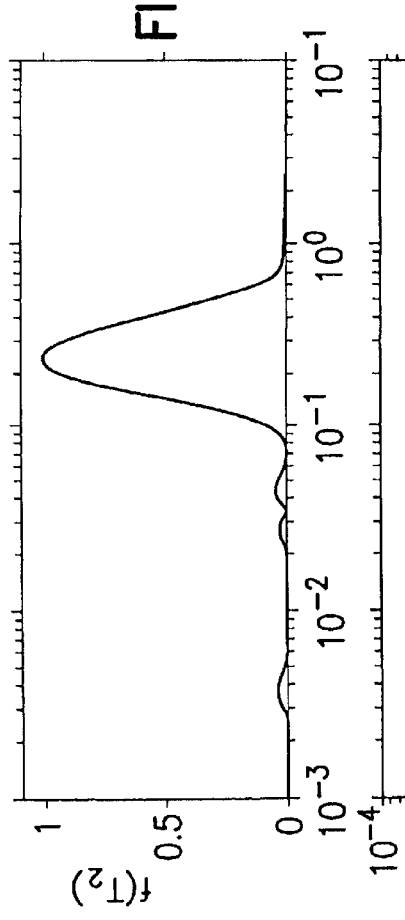
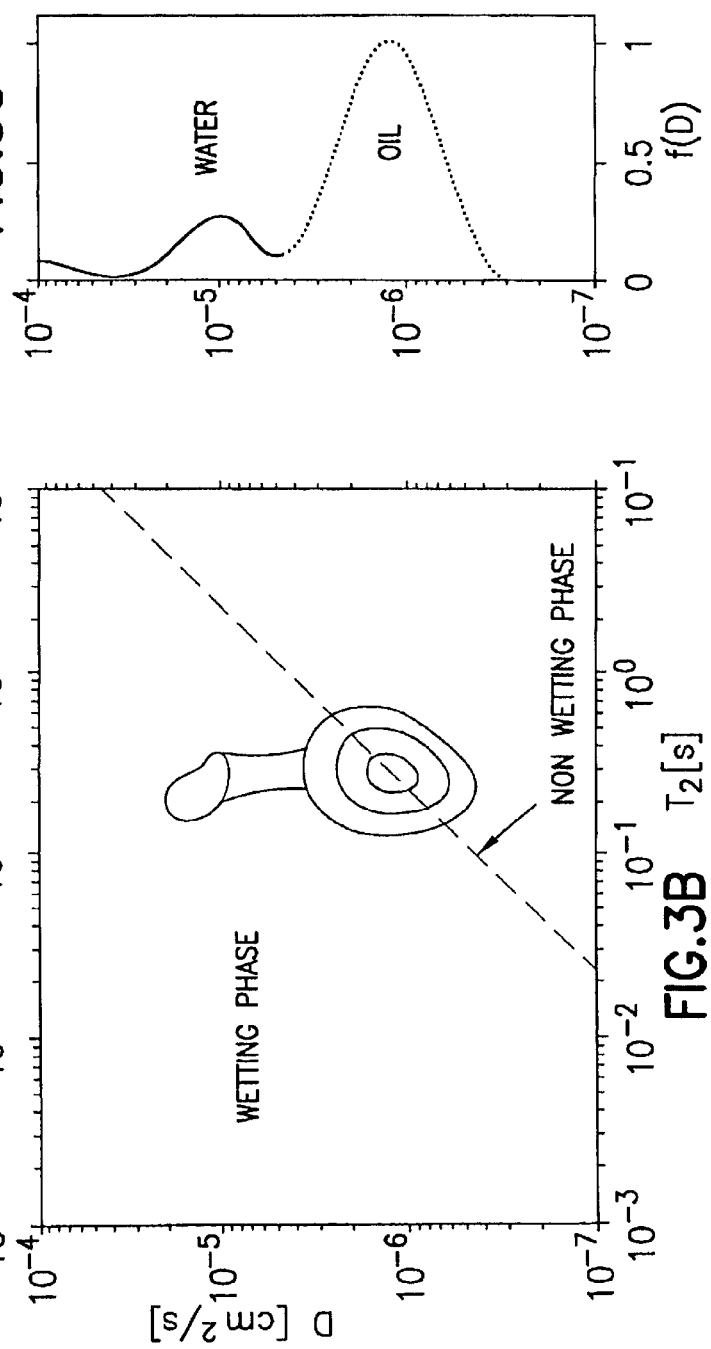

WATER SATURATED

DRAINAGE

IMBIBITION

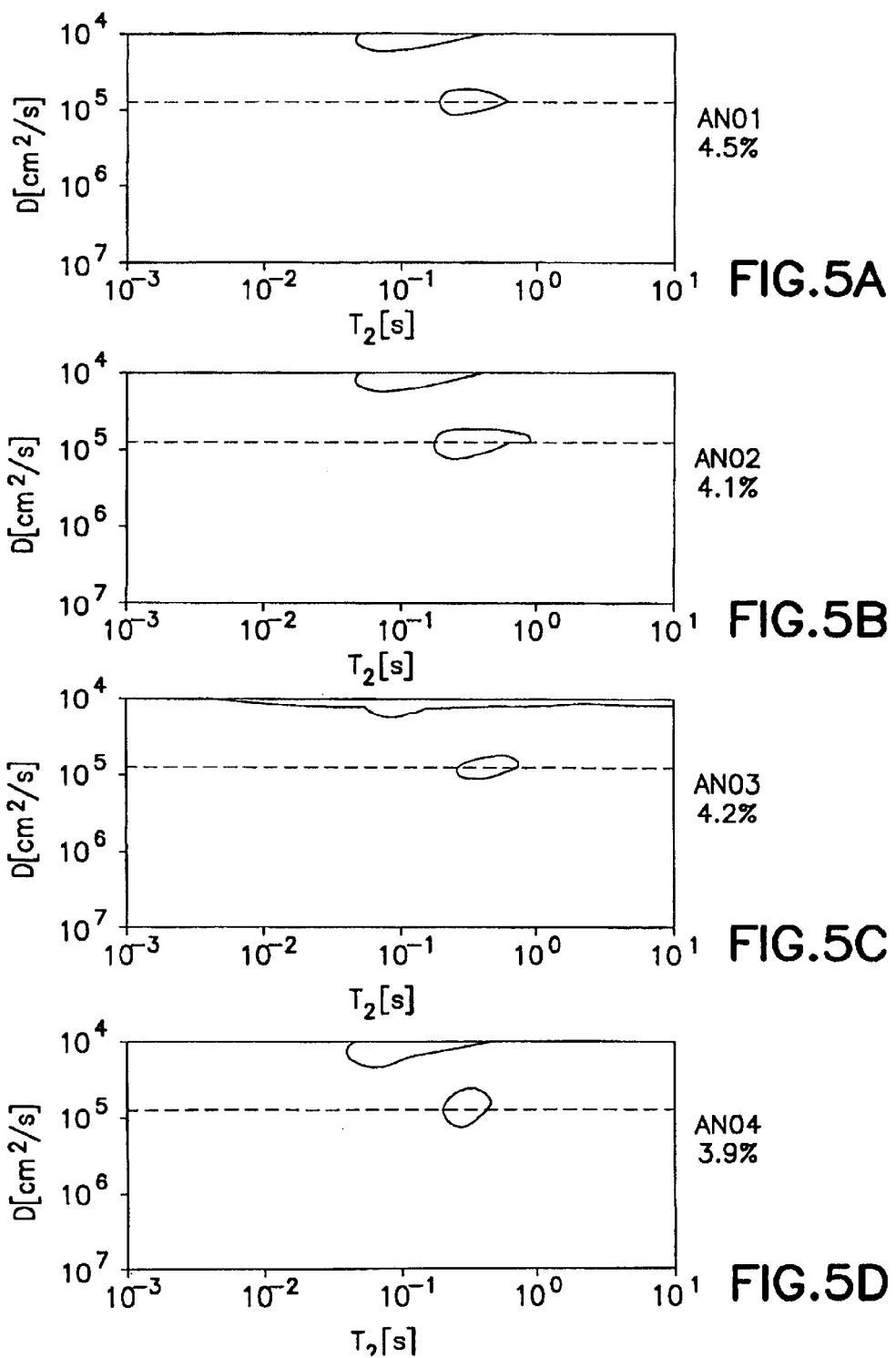

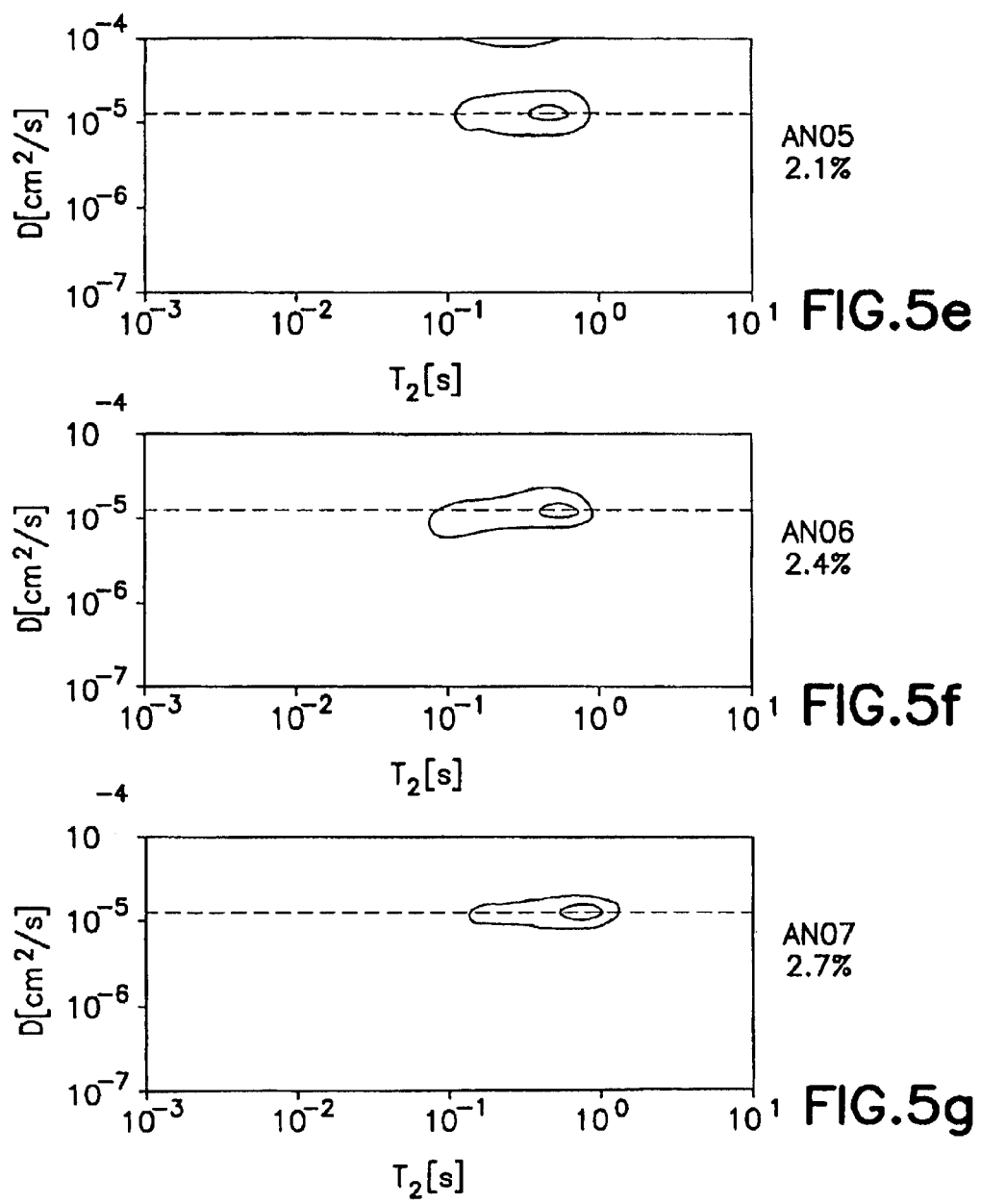

METHOD AND APPARATUS FOR NMR MEASUREMENT OF MAGNETIC MATERIALS

This patent application claims priority from U.S. Provisional Application No. 60/440,476 filed on Jan. 16, 2003, which is incorporated herein by reference in its entirety.

FIELD OF THE INVENTION

The present invention relates to the use of nuclear magnetic resonance (NMR) diffusion-editing as an indicator of the presence of magnetic materials in a porous media, and more particularly, to the detection of magnetic minerals in a region of earth formation.

BACKGROUND

NMR has been a common laboratory technique for over forty years and has become an important tool in formation evaluation. General background of NMR well logging can be found, for example, in U.S. Pat. No. 5,023,551 to Kleinberg et al., which is assigned to the same assignee as the present invention and herein incorporated by reference in its entirety.

NMR relies upon the fact that the nuclei of many chemical elements have angular momentum ("spin") and a magnetic moment. In an externally applied static magnetic field, the spins of nuclei align themselves along the direction of the static field. This equilibrium situation can be disturbed by a pulse of an oscillating magnetic field (e.g., a radio frequency (rf) pulse) that tips the spins away from the static field direction. The angle through which the spins are tipped is given by $\theta = \gamma B_1 t_p / 2$, where $\gamma$ is the gyromagnetic ratio, $B_1$, is the linearly polarized oscillating field strength, and $t_p$ is the duration of the pulse. Tipping pulses of 90 and 180 degrees are most common.

After tipping, two things occur simultaneously. First, the spins precess around the direction of the static field at the Larmor frequency, given by $\omega_0 = \gamma B_0$, where $B_0$ is the strength of the static field and $\gamma$ is the gyromagnetic ratio. For hydrogen nuclei, $\gamma/2\pi = 4258$ Hz/Gauss, so, for example, in a static field of 235 Gauss, the hydrogen spins would precess at a frequency of 1 MHz. Second, the spins return to the equilibrium direction according to a decay time, $T_1$, which is known as the spin-lattice relaxation time.

Also associated with the spin of molecular nuclei is a second relaxation time, $T_2$, called the spin-spin relaxation time. At the end of a 90-degree tipping pulse, all the spins are pointed in a common direction perpendicular, or transverse, to the static field, and they all precess at the Larmor frequency. However, due to small fluctuations in the static field induced by other spins or magnetic impurities, the spins precess at slightly different frequencies, and the transverse magnetization dephases with a time constant $T_2$.

A standard technique for measuring $T_2$, both in the laboratory and in well logging, uses an RF pulse sequence known as the CPMG (Carr-Purcell-Meiboom-Gill) sequence. As is well known, after a wait time that precedes each pulse sequence, a 90 degree pulse causes the spins to start precessing. Then, at time $t_E/2$, a 180 degree pulse is applied that keeps the spins in the transverse plane but causes the spins, which have been dephasing to refocus at a time $t_E$ after the initial 90 degree pulse. By repeatedly manipulating the spins using a series of 180 degree pulses, a series of "spin echoes" appear. The train of echoes is measured and processed to determine the irreversible dephasing, $T_2$.

In rock formations, such as in a borehole environment, $T_2$ for hydrogen-containing fluids (such as water, oil, gas) can have significant contributions due to surface relaxation, bulk relaxation, and diffusion effects, i.e., $$\frac{1}{T_2} = \frac{1}{T_{2,surface}} + \frac{1}{T_{2,bulk}} + \frac{1}{T_{2,diffusion}} \qquad (1)$$

Each of these contributions provides some information about the rock formation and/or about the fluid in the rock formation.

In a uniform static magnetic field, each spin will experience the same magnetic field strength regardless of its position within the static field, and diffusion will not contribute to the observed $f(T_2)$. In a magnetic field gradient, however, each spin will experience different magnetic field strengths as it diffuses through the static field. The Larmor frequencies of the diffusing spins become time dependent, and the series of 180 degree pulses cannot refocus the spins completely, leading to an additional decay signal. This additional decay signal is proportional to the diffusion coefficient, D, of the fluid and to the square of the gradient strength, g, and the square of the echo spacing, $t_E$, i.e., $$\frac{1}{T_{2,diffusion}} = \frac{1}{12} \gamma^2 g^2 D t_E^2 \qquad (2)$$

Because the diffusion coefficient provides an indication of fluid type, measurement of the diffusion effects on $f(T_2)$ has been used as the basis for determining the types of fluids in a rock formation.

Certain NMR measurements of diffusion involve changing the echo spacing, $t_E$, in a standard CPMG sequence, and thus the amount of diffusion the spins undergo between echoes, and then comparing the measured relaxations. FIGS. 1(a) and 1(b) generally illustrate this approach. FIG. 1(a) shows two CPMG sequences with different echo spacings, $t_1$ and $t_2$, where $t_2$ is longer than $t_1$. As the echo spacing increases, the spins diffuse further between echoes, and the measured relaxation times will decrease depending on the diffusion coefficient of the fluid, as given in Equation (2) above. FIG. 1(b) shows the relaxation distributions, $f(T_2)$, for an oil and water determined from the two sets of echoes acquired from the two CPMG sequences illustrated in FIG. 1(a). As seen in FIG. 1(b), the relaxation distribution with the longer echo spacing, $t_2$, is shifted to lower relaxation times, $T_2$, relative to the relaxation distribution with the shorter echo spacing, $t_1$. The size of the shift is proportional to the size of the diffusion coefficient, as indicated by arrows 1 and 2. The shift of $f(T_2)$ for a fluid with a small diffusion coefficient 1, such as heavy oil, is smaller than the shift for a fluid with a larger diffusion coefficient 2, such as water or natural gas.

While such NMR diffusion measurements can be useful, they suffer from a number of drawbacks. For example, the presence of materials with discernible magnetic susceptibility in a porous media under investigation, such as paramagnetic and ferromagnetic minerals in a region of earth formation, has been known to compromise NMR results. For example, chlorite is a pore-lining clay and can be an important indicator of reservoir quality. The presence of chlorite is often strongly correlated with reservoir properties, such as porosity and permeability. Chlorite is paramagnetic mineral and, therefore, can create locally high internal field gradients. These field gradients may shift the diffusion contribution of hydrocarbon during nuclear magnetic resonance (NMR) analysis so that it appears to be water. As a result, hydrocarbon reservoirs may be overlooked because they were improperly identified as water during conventional NMR logging. Further, reservoirs in chlorite deposits are relatively easily extracted due to the physical/chemical properties of chlorite as compared to other mineral deposits. To date, there has been no effective method of determining the presence of materials with discernible magnetic susceptibility.

Accordingly, it is an object of the present invention to provide an NMR method that adequately accounts for the presence of materials with discernible magnetic susceptibility.

It is a further object of the present invention to provide an NMR method as an indicator for the presence and quantity of chlorite and other paramagnetic and ferromagnetic minerals in an earth formation.

SUMMARY OF THE INVENTION

Commonly owned U.S. Pat. No. 6,570,382, incorporated by reference herein in its entirety, discloses a method called diffusion-editing that is useful in separating diffusion and relaxation effect for determining saturation and pore geometry. The present invention discloses the application of this method to determine the presence and relative quantity of magnetic materials in a porous media. For the purposes of this patent application, "magnetic materials" broadly refers to all materials having discernible magnetic susceptibilities including paramagnetic and ferromagnetic materials. Porous media containing these materials can exhibit larger internal field gradients which influence NMR measurements. Magnetic minerals include, for example, paramagnetic minerals (including, but not limited to, hematite, franklinite, chlorite, glauconite and siderite) and ferromagnetic minerals (including, but not limited to, magnetite and pyrrhortite). While the examples provided below relate to the identification of magnetic minerals in an earth formation, the present invention is equally applicable to any other media containing magnetic materials, including, but not limited to, molecular sieves, biological/medical samples, etc.

In a first embodiment, a method of extracting information about a fluid-containing media is disclosed comprising: (a) applying a magnetic field gradient to the media; (b) applying a first series of oscillating magnetic field pulses to the media, the first series of pulses having an initial magnetic field pulse, a first portion followed by a second portion; (c) detecting magnetic resonance signals generated in (b); (d) after a wait time, applying a second series of oscillating magnetic field pulses to the media, the second series of pulses having an initial magnetic field pulse, a third portion followed by the second portion; (e) detecting magnetic resonance signals generated in (d); and (f) analyzing the detected signals to determine the presence of magnetic materials in the media. The magnetic field gradient may be either a static field gradient or a pulsed field gradient. In analyzing the detected signals, it may be beneficial to separate diffusion and relaxation effects. If (d) and (e) are repeated one or more times, a two-dimensional function describing the diffusion and relaxation of the media may be developed. This function may be used to provide a visual analysis (i.e., a map) of the presence of magnetic materials. Further, a calibration indicative of one or more magnetic materials may be developed in terms of diffusion and relaxation and correlated to the two-dimensional function to assist in determining the presence of magnetic materials in the sample.

To determine the relative content of the magnetic material in the sample, a two-dimensional function (i.e., a D-$T_2$ function) of the porous media is created by repeating (d) and (e) one or more times. A calibration describing the relationship between diffusion and relaxation representative of at least one magnetic material anticipated to be present in the porous media is correlated to the two-dimensional function.

Alternatively, diffusion distributions of the porous media and the fluid in the media are developed. Then the percentage of magnetic resonance signals having a diffusion coefficient higher than the diffusion coefficient of the fluid is calculated. This percentage is representative of the relative content of the magnetic material in the porous media.

In a second embodiment, a logging apparatus is disclosed comprising: a logging tool that is moveable through a borehole and a processor that is coupled with the logging tool The processor is programmed with instructions which, when executed by the processor, cause the logging tool to: (i) generate a first series of oscillating magnetic field pulses to a region of earth formation, the first series having an initial magnetic field pulse, a first portion followed by a second portion; and (ii) detect magnetic resonance signals produced from the region of earth formation; (iii) after a wait time, apply a second series of oscillating magnetic field pulses to the region of earth formation, the second series having an initial magnetic field pulse, a third portion followed by the second portion; and (iv) detect magnetic resonance signals produced from the region of earth formation. The instructions further cause the processor to: (v) analyze the detected magnetic resonance signals to determine the presence of magnetic minerals in the region of investigation. The instructions further provide for (1) the separation diffusion and relaxation effects and (2) the determination of the diffusion coefficient of the region of earth formation. The instructions may be programmed to cause the logging tool to repeat (iii) and (iv) above one or more times, wherein each additional series of pulses, comprises an initial magnetic field pulse, a modified third portion followed by the second portion. This data may be used to develop a two-dimensional function describing the diffusion and relaxation of the region of earth formation. The processor may be programmed with a calibration function describing the relationship between diffusion and relaxation representative of the presence of one or more magnetic minerals and correlate it to the two-dimensional function.

Further features and applications of the present invention will become more readily apparent from the figures and detailed description that follows.

BRIEF DESCRIPTION OF THE DRAWINGS

FIGS. 3(a)–(c) is a 3-D map based on the two-dimensional D-$T_2$ function for partially saturated Berea sandstone.

FIGS. 5(a)–(g) are diffusion-edited (D-$T_2$) maps of water saturated core samples having varying levels of chlorite, a paramagnetic mineral.

DETAILED DESCRIPTION OF THE INVENTION

Diffusion-Editing Methodology

Figure 1A:
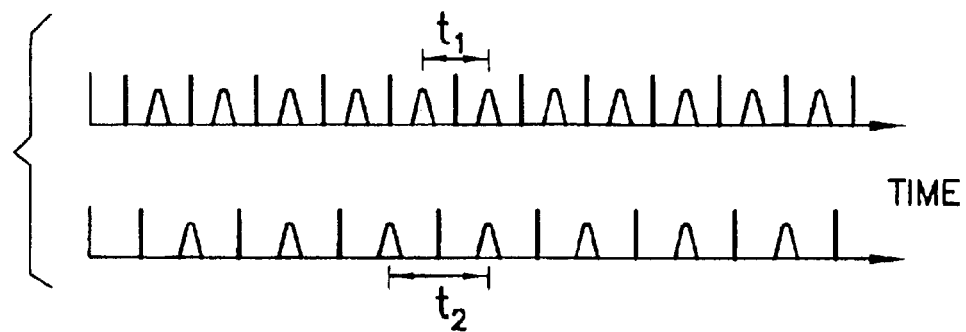
FIGS. 1(a) and (b) taken together, illustrate a NMR measurement and $T_2$ distributions obtained therefrom according to the prior art.
Figure 1B:
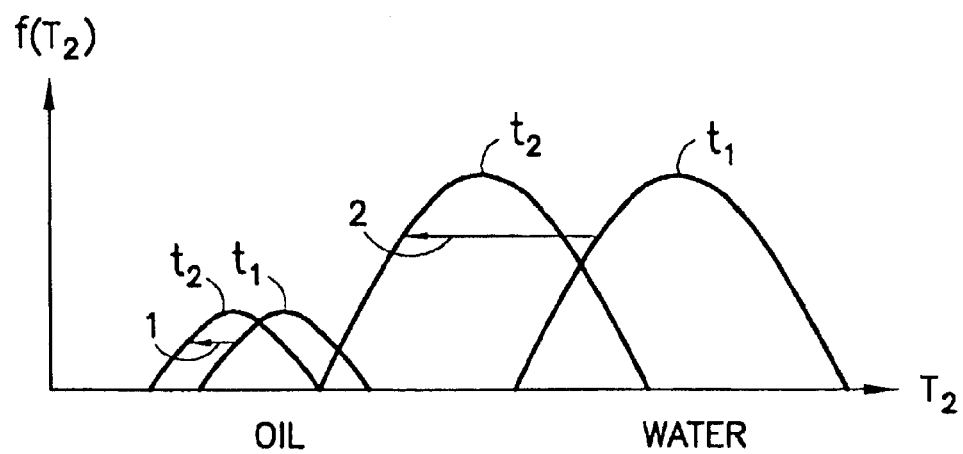
Figure 2A:
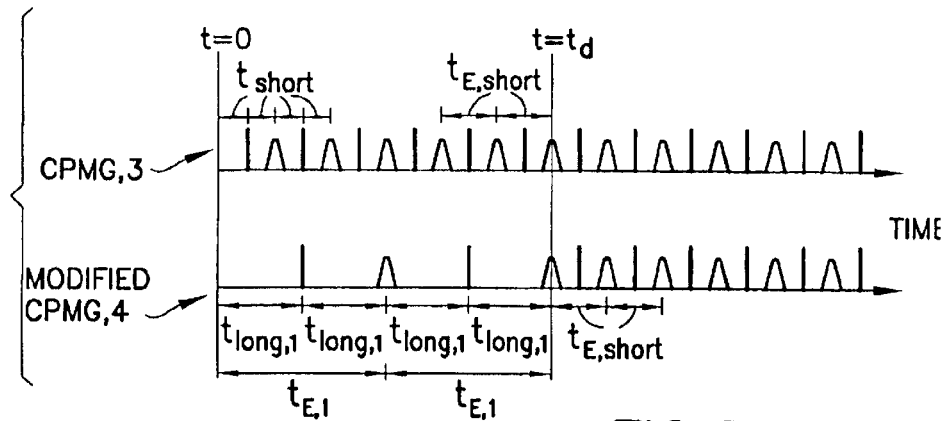
FIGS. 2(a)–(c), taken together, illustrate one embodiment of a NMR measurement and $T_2$ distributions obtained therefrom according to the diffusion-editing technique.
Figure 2B:
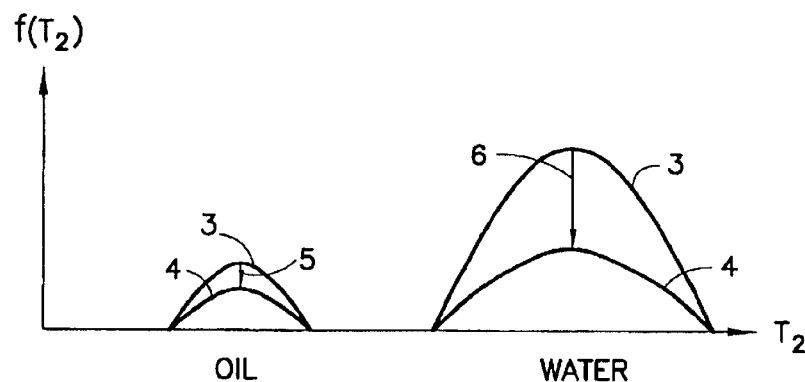
Figure 2C:
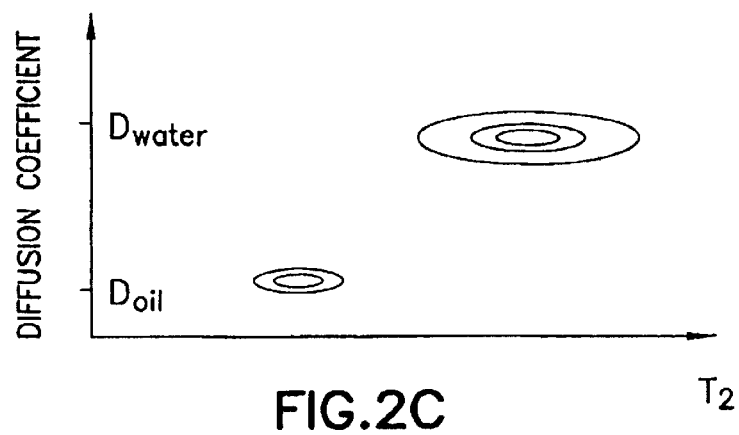

The present invention discloses method that allows identification of the presence and quantity of magnetic material (including ferromagnetic and paramagnetic materials) in a porous media, such as an earth formation. FIGS. 2(a)–(c) describe the diffusion-editing technique, which is further described in commonly owned U.S. Pat. Nos. 6,462,542, 6,522,136 and 6,570,382, U.S. patent application Ser. No. 10/318,798, and the following articles: Hürlimann et al., "The Diffusion-Spin Relaxation Time Distribution as an Experimental Probe to Characterize Fluid Mixtures in Porous Media," *J. Chem. Phys.* 117, 10223–10232 (2002); Hürlimann, et al., "Diffusion-Editing: New NMR Measurement of Saturation and Pore Geometry," SPWLA Proc. 43$^{rd}$ Annual Logging Symposium, Oiso, Japan, Paper FFF (2002); Hürlimann, et al., "Quantitative Measurement of Two-Dimensional Distribution Functions of Diffusion and Relaxation in Grossly Inhomogeneous Fields," *J. Mag. Reson.*, 157, 31–42 (2002). All of these patents, patent applications and articles are incorporated by reference herein in their entireties.

As shown in FIG. 2(a), the first sequence is the standard CPMG sequence with minimal echo spacing $t_E$. In the second sequence, the first two echo spacings are increased to $t_{E,long}$, and then followed by a long train of 180 degree pulses with identical echo spacings $t_E$ as in the first sequence. While it is preferred that two echo spacings are increased, only one or additional echo spacings may also be increased to $t_{E,long}$.

Further, as shown in FIG. 2(a), measurements with the diffusion-editing sequence are compared with measurements using the conventional CPMG sequence. In the diffusion-editing sequence, the first two echo spacings are increased. The echoes after time $t_d$ are used to calculate the $T_2$ distributions for the two measurements, as shown in FIG. 2(b). The relaxation times are identical in both passes, but relative signal amplitudes depend on diffusion. The larger the diffusion coefficient is, the larger the ratio of amplitudes between the distributions. As shown in FIG. 2(c), the data can be expressed as a diffusion-$T_2$ map based on the two-dimensional diffusion-$T_2$ function (i.e. 3-D plot).

The initial time $t_d$ is used to edit the amplitude of the signal according to diffusion. After $t_d$, the two pulse sequences are identical. The observed relaxation times after t>$t_d$ are identical for both sequences shown in FIG. 2(b). However, the relative amplitude of each $T_2$ component depends on the extra diffusive decay during the interval $t_d$. Compared to the first sequence, the signal of the second sequence has an amplitude that is diffusion-edited at $t_d$ according to the diffusion coefficient of the fluid. The ratio of the amplitudes of the $T_2$ distribution depends only on diffusion because surface and bulk relaxation during $t_d$ affects the signal in the two sequences the same way. The signal for times t larger than $t_d$ is given by:

$$M(t_{E,long}, t) \approx \int\int dD dT_2 f(D, T_2) e^{-t/T_2} \exp\left\{-\frac{1}{6}\gamma^2 g^2 D t_{E,long}^3\right\} \quad (4)$$

Here $f(D,T_2)$ is the two-dimensional diffusion-$T_2$ probability density function. Note that the kernel in Equation (4) separates into two terms: (1) $e^{-t/T_2}$ only depends on the experimental time t and the parameter $T_2$; and $$\exp\left\{-\frac{1}{6}\gamma^2 g^2 D t_{E,long}^3\right\} \quad (2)$$

only depends on the different (increased) experimental time $t_{E,long}$ and the parameter D. By measuring the signal for different initial echo spacings $t_{E,long}$, it is therefore possible to extract diffusion coefficient and relaxation time separately.

In practice, the echo spacing after $t_d$ is chosen as short as possible for optimal signal-to-noise ratio and to minimize the diffusion effects on the measured values of $T_2$. If passes with two different values of initial echo spacings are used (as shown in FIGS. 2(a)–(c)), it is possible to extract at every relaxation time $T_2$ an average diffusion coefficient.

If more than two different initial echo spacings are used, it is possible to extract a distribution of diffusion coefficients for every $T_2$, resulting in a full D-$T_2$ map. There is a straightforward trade-off between the resolution in D and the required number of measurements with different diffusion-editing.

In essence, the minimum diffusion-edited pulse sequence may be described as:

| | A | | B | | (5a) |
|---|---|---|---|---|---|
| | ← $t_d$ → | | | | |

| | A | | B | | (5b) |
|---|---|---|---|---|---|
| | ← $t_d$ → | | | | |

One or more additional sequences may be used to develop a 2-D function and thereby create a 3-D plot (as shown in FIG. 3):

| | A″ | | B | | (5c) |
|---|---|---|---|---|---|
| | ← $t_d$ → | | | | |

| | A‴ | | B | | (5d) |
|---|---|---|---|---|---|
| | ← $t_d$ → | | | | |

Diffusion-Editing to Determine the Presence/Quantity of Magnetic Materials

It has been discovered that the diffusion editing method described above may be used to account for the presence of magnetic material in a porous media. Further, the method may be used to quantify the relative amount of magnetic materials present in a given sample or region of investigation. By developing a calibration curve representative of a response of a magnetic material to an NMR signal, NMR data may be analyzed to taking into account any internal field gradients created by the presence of a magnetic material.

In a preferred embodiment, the relative content of the magnetic material in a porous media may be determined by developing a two dimensional function (i.e., a D-$T_2$ function) of the porous media using diffusion editing. A calibration function describing the relationship between diffusion and relaxation representative of at least one magnetic material anticipated to be present in the porous media is developed. This calibration function can be diffusion-edited function, a relaxation curve or a diffusion distribution of the magnetic material anticipated to be present in the sample. When correlated to the two-dimensional function of the sample, the calibration function will identify the presence of (and relative quantity of) magnetic material in the sample under investigation.

The method may also be employed if no (or little) information is known about a fluid-containing porous media a priori. For example, diffusion distributions of the porous media and the fluid in the media are developed. Then the percentage of magnetic resonance signals having a diffusion coefficient higher than the diffusion coefficient of the fluid is calculated. This percentage is representative of the relative content of the magnetic material in the porous media.

EXAMPLE

The non-limited example presented below describes the identification and quantification of chlorite, a paramagnetic mineral, in an earth formation. This example is provided for illustration purposes only and is not intended to limit the scope of the present invention. One skilled in the art would recognize the applicability of this methodology to any sample that may contain a magnetic material.

Various cores having varying amounts of chlorite were prepared in different saturation states. NMR measurements were performed using the standard Carr-Purcell-Meiboom-Gill (CPMG) pulse sequence and the diffusion-editing method described above. This procedure generally results in more reliable $S_w$ values and can also be used to derive an indicator of chlorite content. Because the measurement of diffusion-editing can be performed with logging tools, this technique can be used directly in a reservoir for the improved determination of saturation and to estimate the chlorite content, with important implications for the assessment of reservoir quality. Alternatively, cores may be brought to the surface for analysis.

When samples are saturated with a mixture of refined oil and brine, it is generally difficult to separate the contributions of the two phases in the CPMG relaxation measurements. The relaxation time of the oil often overlaps significantly with the $T_2$ distribution of the brine signal. To overcome this problem, diffusing-editing may be used to obtain simultaneously diffusion and relaxation information and its correlation. This is achieved by preceding the standard short-echo-spacing CPMG sequence by an editing sequence that attenuates the amplitude of the signal according to diffusion in the applied gradient. Diffusion-editing is implemented by increasing the first two echo spacings systematically. Relaxation information is obtained from the signal decay after the diffusion encoding. This effectively orthogonalizes the diffusion and relaxation information and allows the extraction of diffusion-relaxation distribution functions. These two-dimensional D-$T_2$ maps can be used to extract information about important reservoir parameters such as water saturation, oil viscosity, wettability state and hydrocarbon-corrected bound-fluid volume.

For the samples with low chlorite concentration, the diffusion-relaxation distribution function clearly separates the signal into oil and water contributions. For samples with higher chlorite concentrations, the D-$T_2$ maps show an additional significant contribution at apparent diffusion coefficients in excess of bulk oil or water. In these samples, the presence of chlorite gives rise to internal gradients in the adjacent pore space that exceeds the externally applied gradient. This leads to an increased diffusive decay that can be characterized by a large apparent diffusion coefficient. Chlorite concentration in the sample is well correlated with the fraction of signal that exhibits such large apparent diffusion coefficients.

Figure 4A:
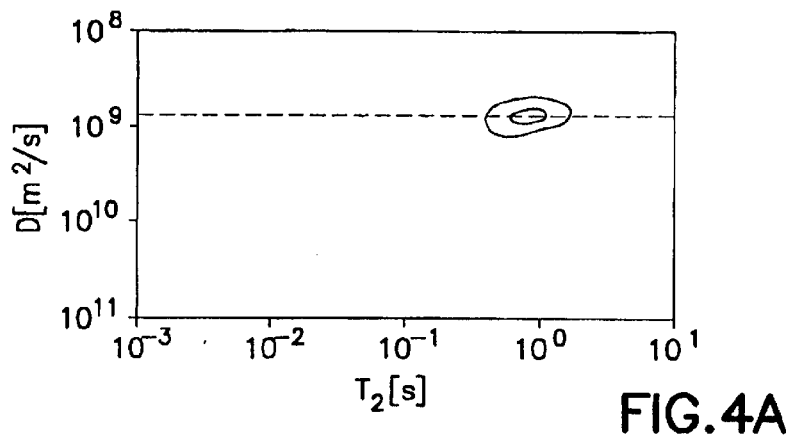
FIGS. 4(a)–(c) are diffusion-edited (D-$T_2$) maps of a core sample with no magnetic materials at different saturation states.
Figure 4B:
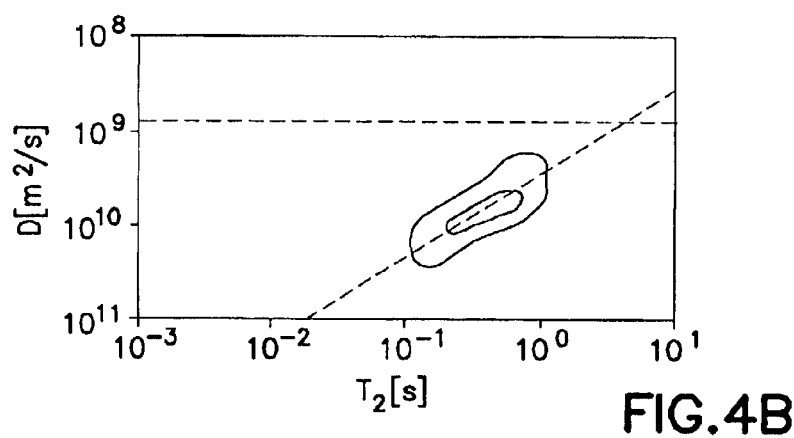
Figure 4C:
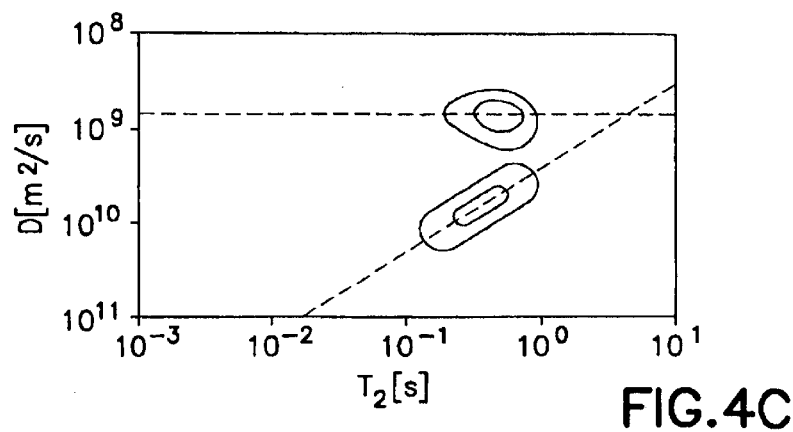

FIGS. 4(a)–(c) are D-$T_2$ maps developed using the diffusion-editing technique for a Bentheimer Sandstone core sample in three different saturation states. FIG. 4(a) shows a fully water saturated sample wherein the D-$T_2$ results lie along the water line. In FIG. 4(b), water that has been drained from the sample has been replaced with crude oil. Accordingly, the D-$T_2$ results lie along the oil line. In FIG. 4(c) the sample has been placed in water and contributions are evident along both the water line and the oil line. FIGS. 4(a)–(c) are typical maps, representing the reference core with no magnetic material, in this case chlorite.

Core samples, AH01 through AH07, having different chlorite content, were analyzed using NMR diffusion-editing. These samples were water saturated so that the D-$T_2$ results lie along the water line, as shown in FIG. 5. However, the D-$T_2$ maps of samples AH01–AH04 show a signal above the water signal indicating a locally higher field gradient. This increased gradient was determined to be caused by the presence of chlorite. As shown in FIG. 5, samples AH01–AH04 have a higher chlorite content (4.5%, 4.1%, 4.2% and 3.9%, by weight, respectively) than samples AH05–AH07 (2.1%, 2.4%, and 2.7%, by weight, respectively) and accordingly show a diffusion contribution above the water line. Samples AH05–AH07, by contrast, shown only a minor contribution in this area.

Figure 6A:
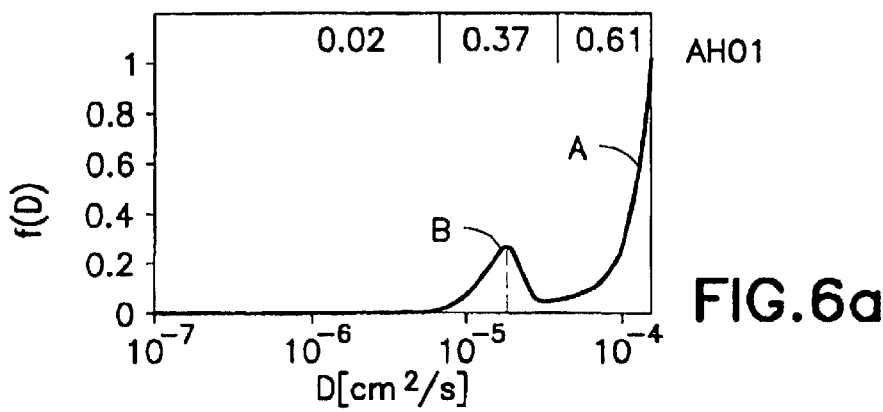
FIGS. 6(a)–(h) are distributions of apparent diffusion coefficient, f(D), for chlorite-containing samples (a)–(g) and a reference sample without chlorite (h).
Figure 6B:
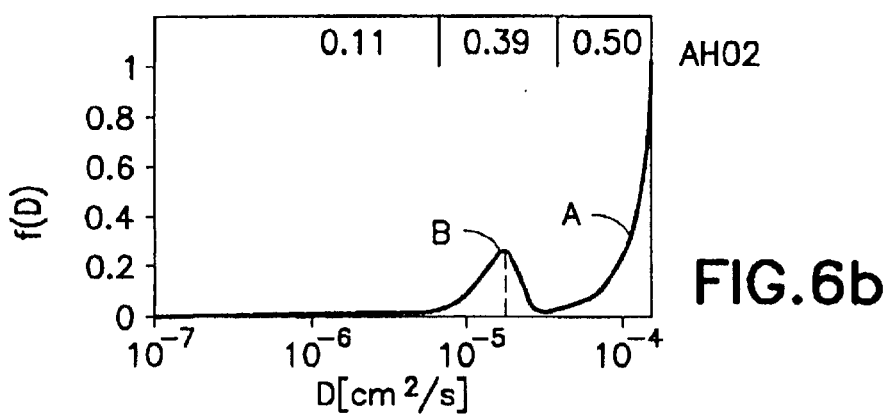
Figure 6C:
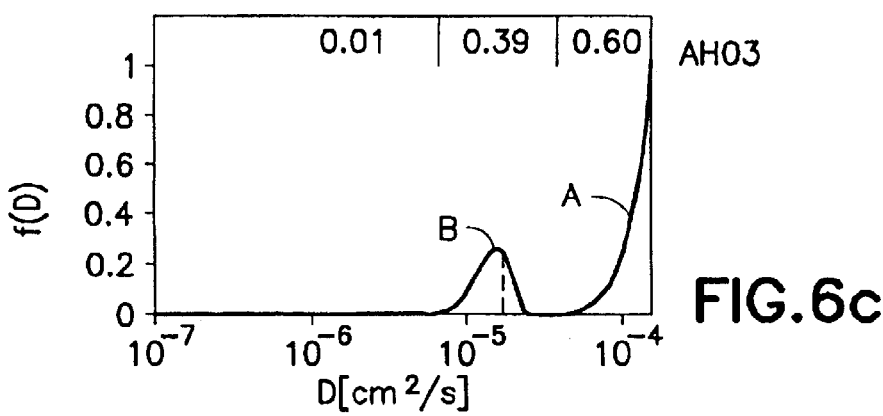
Figure 6D:
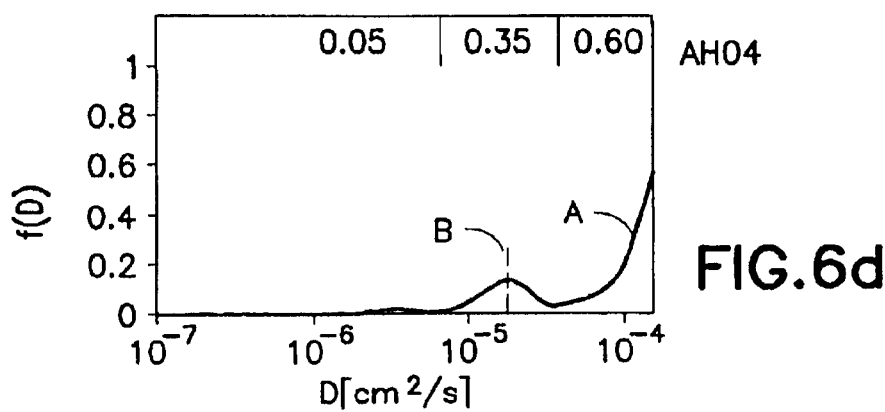
Figure 6E:
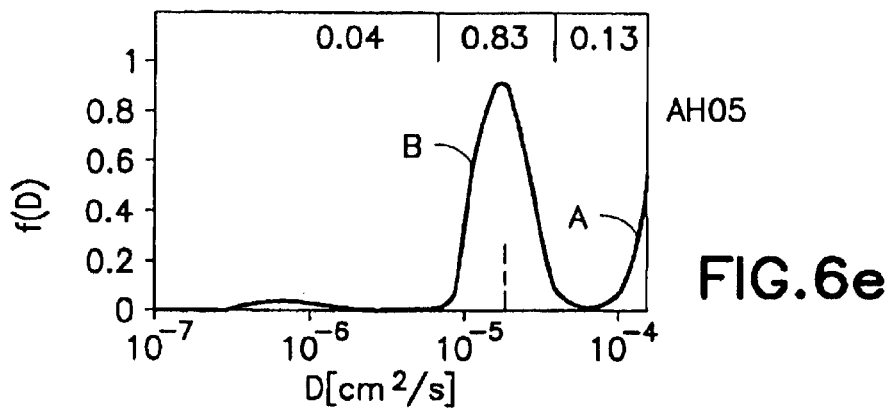
Figure 6F:
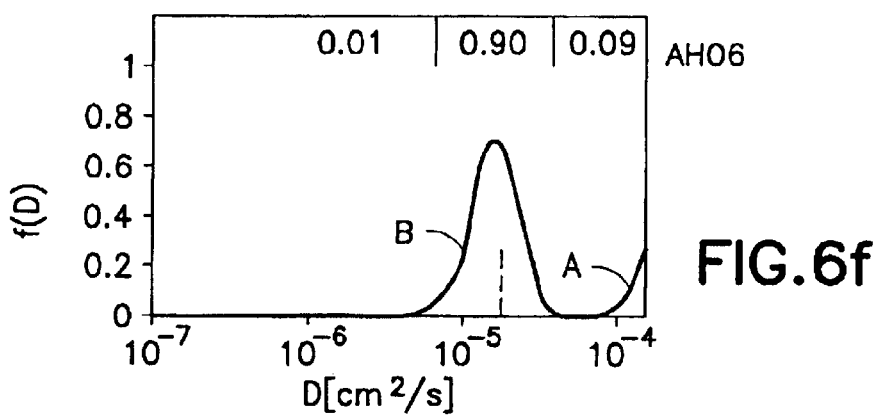
Figure 6G:
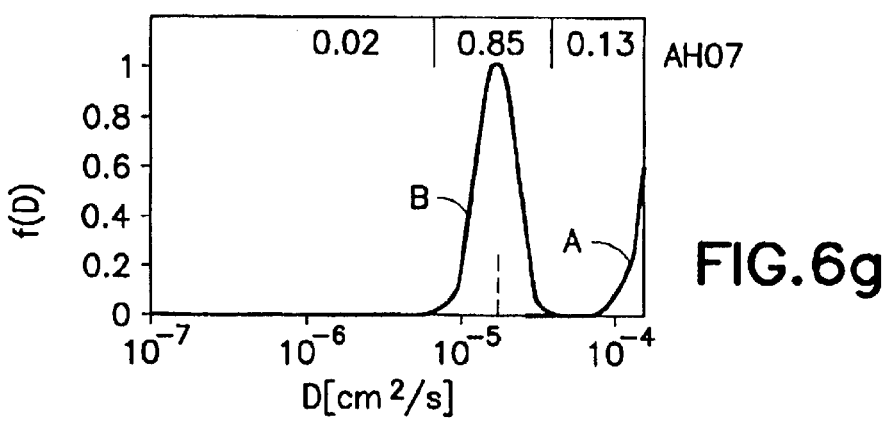
Figure 6H:
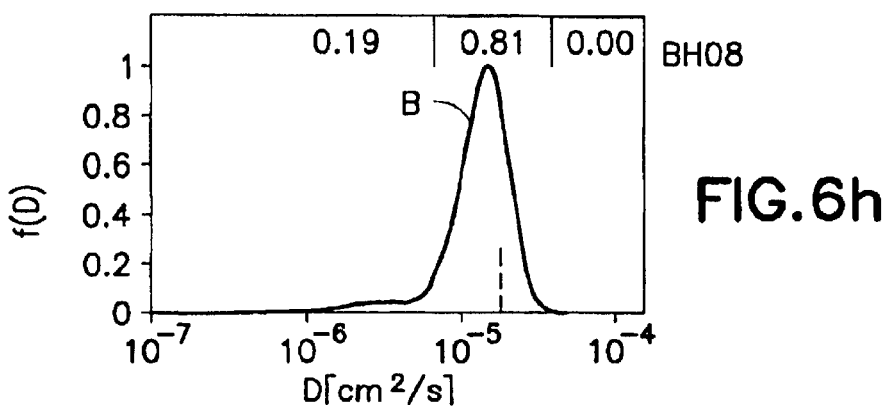

The chlorite signal of samples AH01–AH07 is shown in the diffusion distributions of FIG. 6(a)–(g). In each of these distributions, the chlorite signal is represented by peak A, while the water signal is represented by peak B. By contrast, the diffusion distribution of a reference core known to have no chlorite is shown in FIG. 6(h). This distribution only has peak B corresponding to the presence of water; there is no second chlorite peak.

Figure 7A:
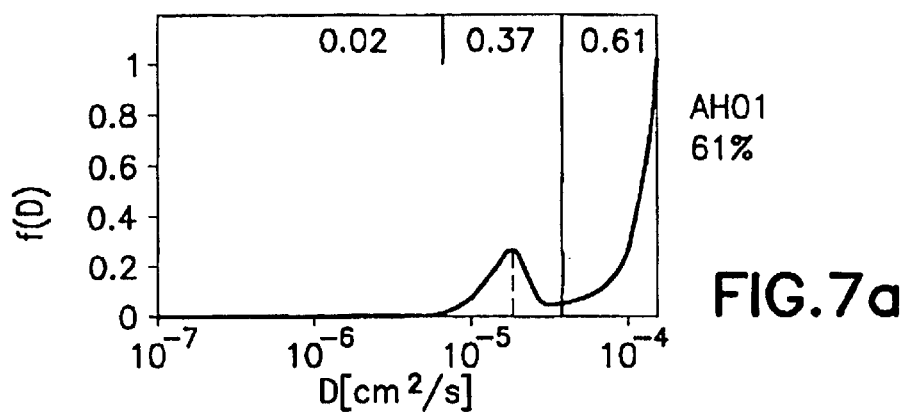
FIGS. 7(a)–(i) are diffusion distributions showing the calculation of weight percentage of chlorite in various samples having different percentages of chlorite content.
Figure 7B:
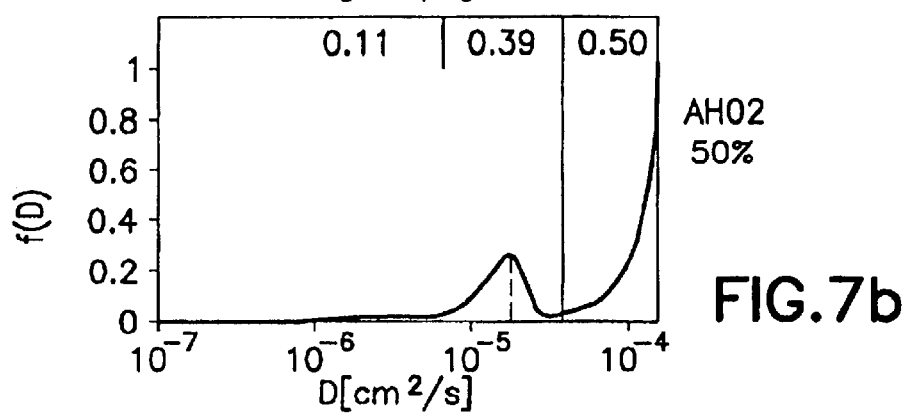
Figure 7C:
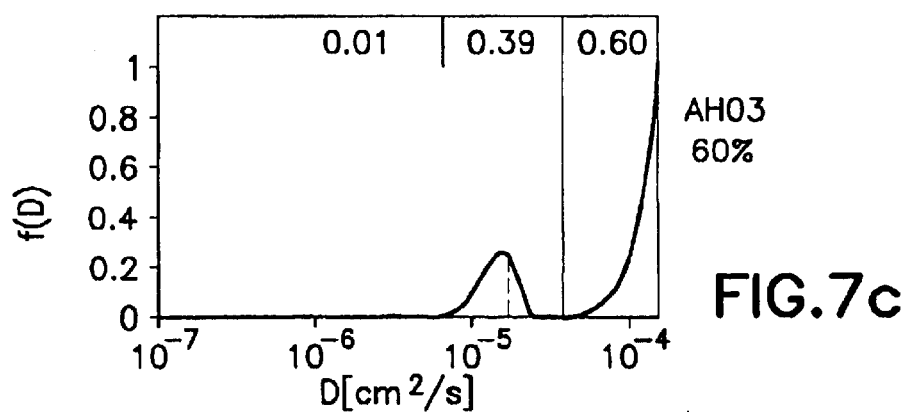
Figure 7D:
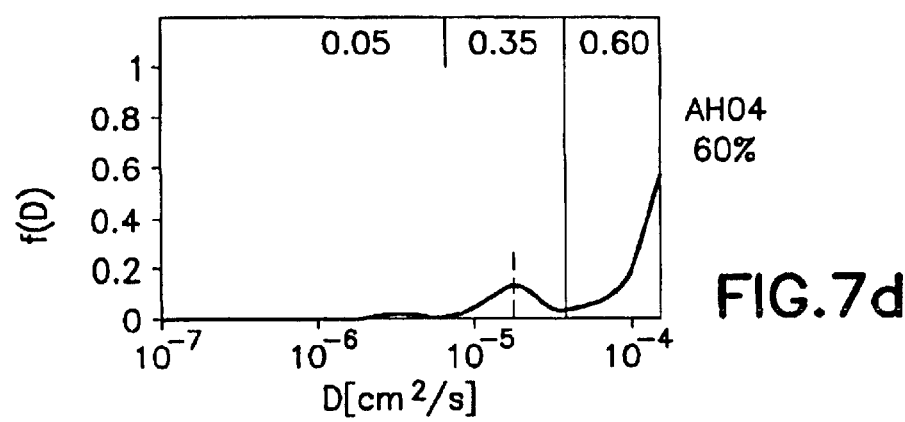
Figure 7E:
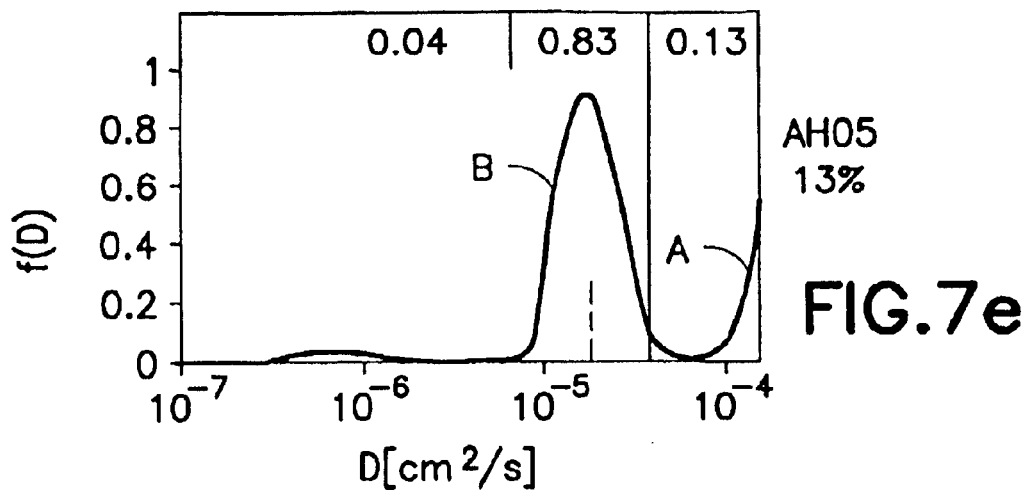
Figure 7F:
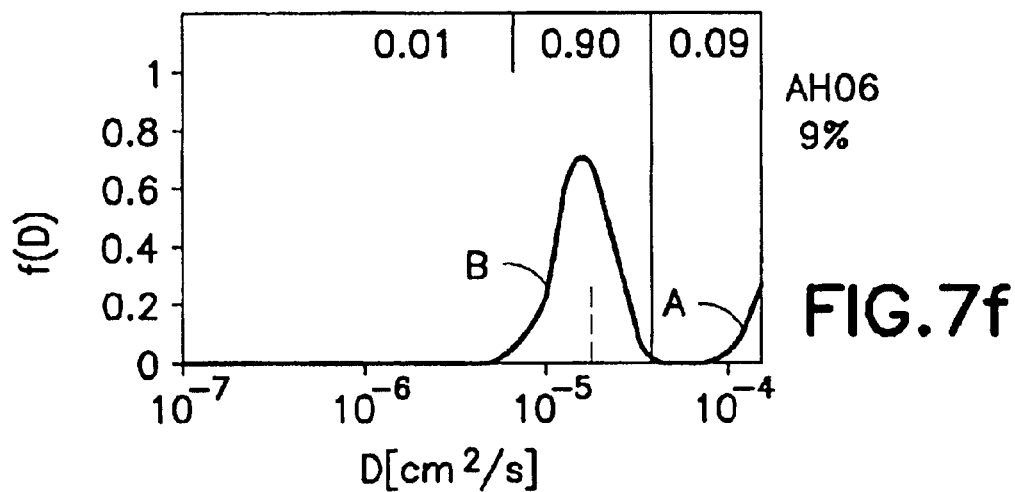
Figure 7G:
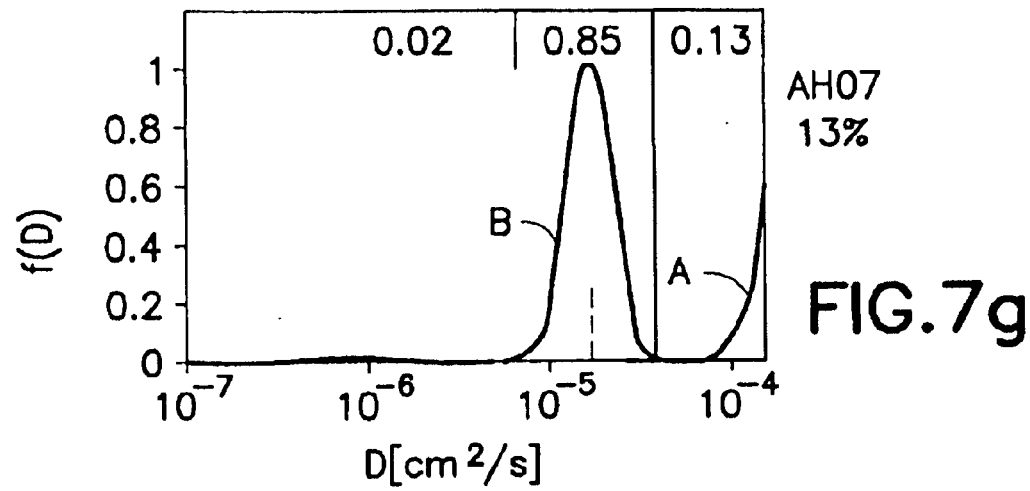
Figure 7H:
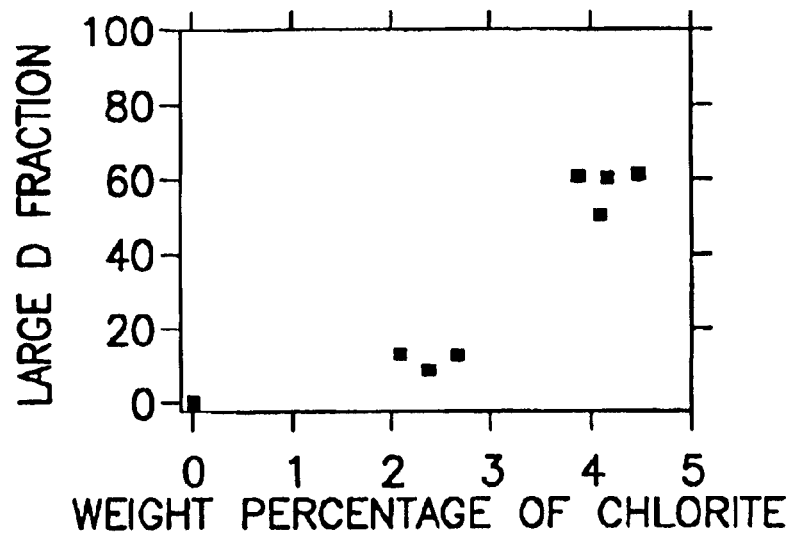
Figure 7I:
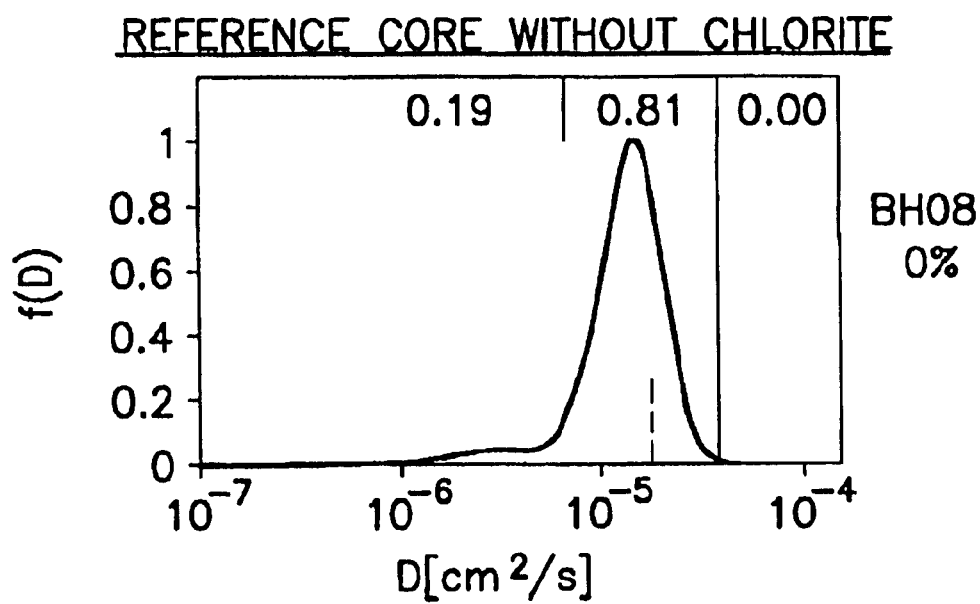

As shown in FIGS. 7(a)–(i), the weight percentage of chlorite may be calculated by determining the area under the second peak of the diffusion distribution (e.g., integrating the diffusion distribution for the second peak) and determining the diffusion fraction associated with the chlorite peak. For example, in sample AH01 60% of the diffusion distribution is associated with the chlorite peak, while in sample AH06 only 9% is associated with the chlorite peak. By contrast, in the reference core known to have no chlorite, there is no chlorite peak and the diffusion fraction is 0%, as shown in FIG. 7(i).

Figure 8A:
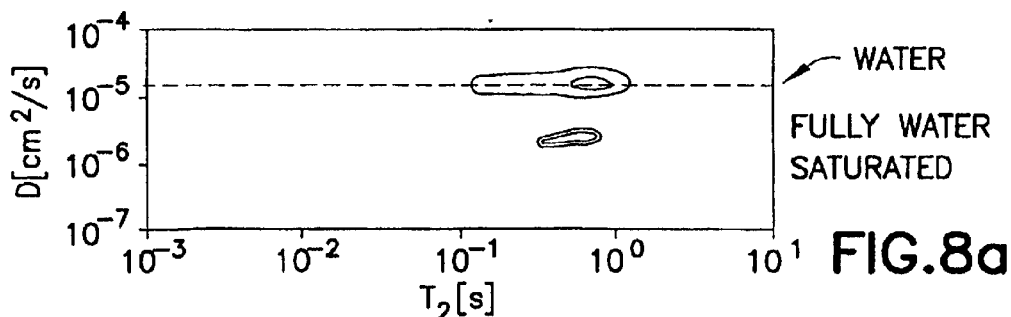
FIGS. 8(a)–(c) are diffusion-edited (D-$T_2$) maps of a core sample with chlorite at various saturation states.
Figure 8B:
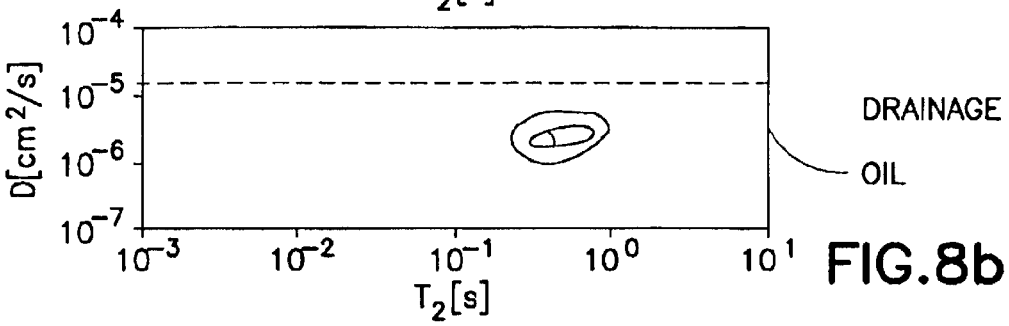
Figure 8C:
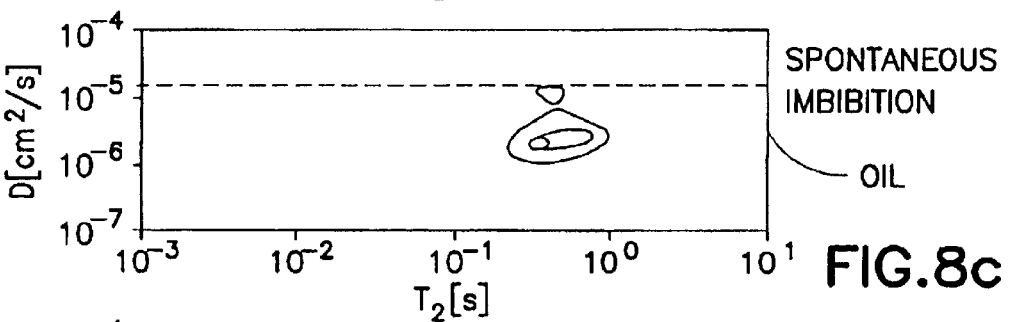
Figure 8D:
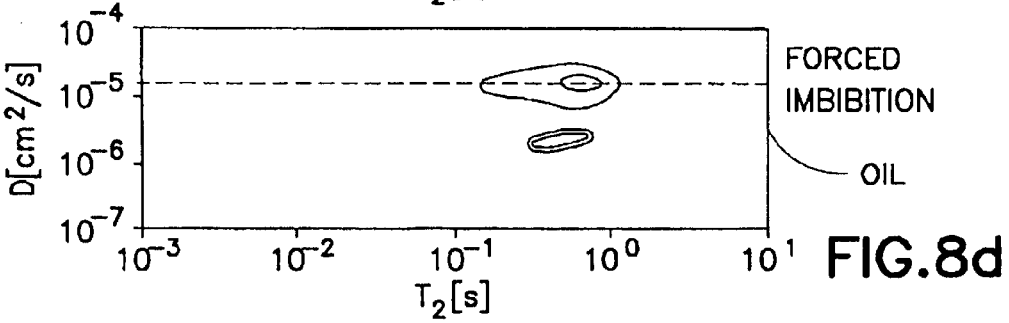
Figure 8E:
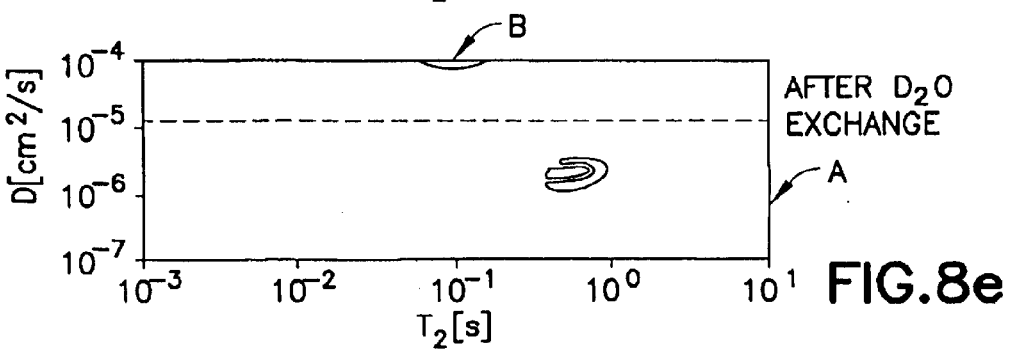

While the samples discussed above relate to the water saturated samples, this method is equally applicable to hydrocarbon-containing samples. As shown in FIGS. 8(a)–(e), the chlorite contribution may be detected and quantified in a hydrocarbon-containing sample using the diffusion-editing technique. FIG. 8(a) is a D-$T_2$ map wherein the core sample is fully water saturated. This map shows water contribution and a small chlorite contribution. In FIG. 8(b), water that has been drained from the core has been replaced with oil. Accordingly, an oil contribution is now visible. FIGS. 8(c) and (d) are the D-$T_2$ maps for the sample after spontaneous and forced imbibition of water (brine), respectively. In FIG. 8(e), the water was masked using $D_2O$ exchange. FIG. 8(e) clearly shows an oil contribution, A, and a chlorite contribution, B. Accordingly, chlorite signal is visible in the presence of hydrocarbons.

Exemplary Apparatus

Figure 9:
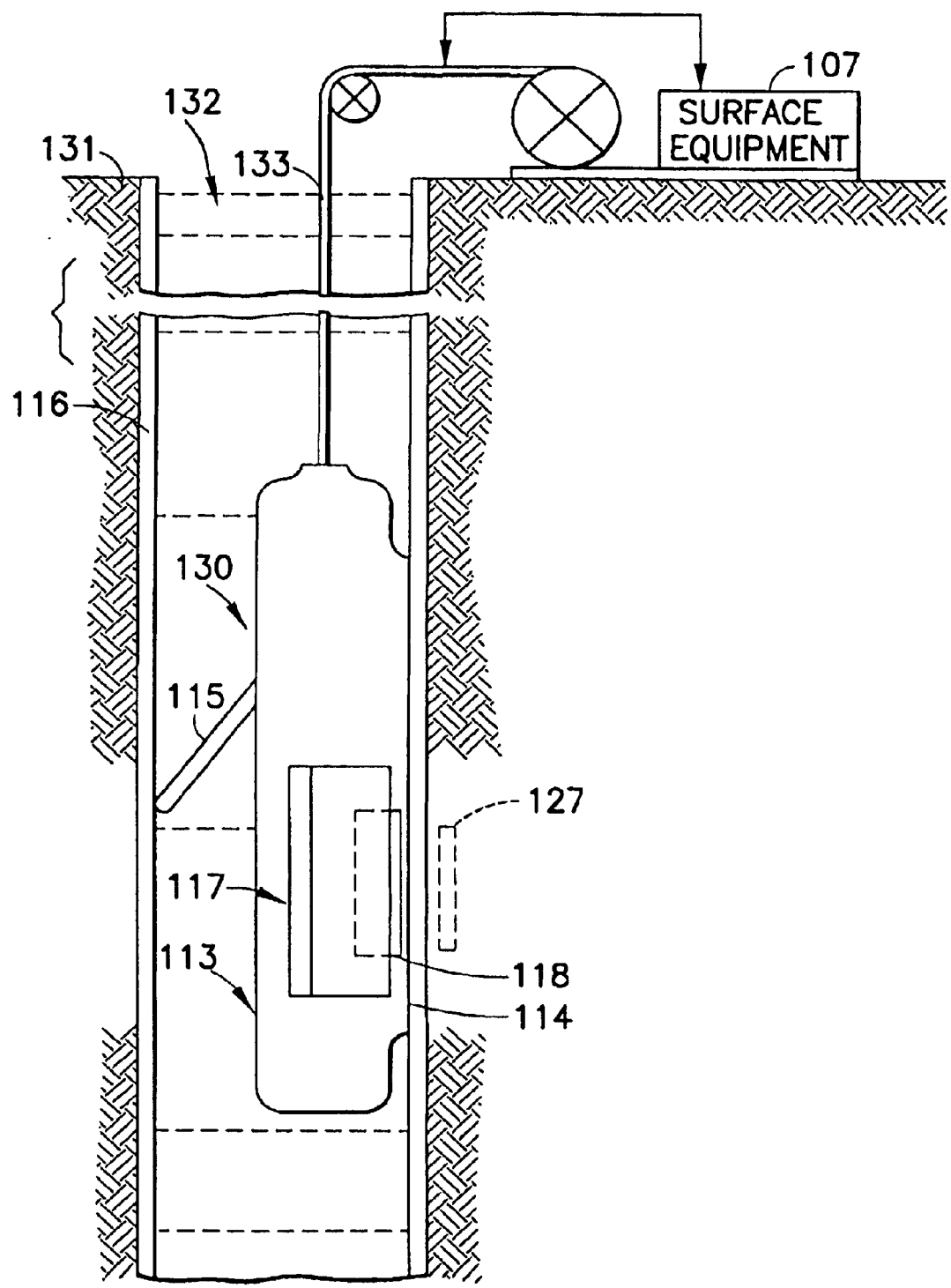
FIG. 9 is a schematic diagram, partially in block form, of one embodiment of a well logging apparatus that can be used in implementing methods according to the invention in a borehole environment.

The methods of the invention may be practiced in a laboratory setting, such as in a medical laboratory, or in a downhole environment, such as with a well logging device. FIG. 9 shows an non-limiting apparatus that can be utilized for practicing embodiments of the invention to investigate subsurface formations 131 traversed by a borehole 132. A magnetic resonance investigating apparatus or logging device 130 is suspended in the borehole 132 on an armored cable 133, the length of which substantially determines the relative depth of the device 130. The length of cable 133 is controlled by suitable means at the surface such as a drum and winch mechanism. Surface equipment, represented at 107, can be of conventional type, and can include a processor subsystem that communicates with all the downhole equipment. It will be understood that some of the processing can be performed downhole and that, in some cases, some of the processing may be performed at a remote location. Also, while a wireline is illustrated, alternative forms of physical support and communicating link can be used, for example in a measurement-while-drilling or logging-while-drilling system, in practicing the methods of the invention.

As described, for example, in U.S. Pat. Nos. 5,055,787, 5,055,788, and 5,153,514, the magnetic resonance logging device 130 can have a face 114 to intimately contact the borehole wall. The borehole wall may have a mudcake 116 thereon. A retractable arm 115 is provided which can be activated to press the body of the tool 113 through the mudcake against the borehole wall during a logging run, with the face 114 pressed against the wall's surface. Although the tool 113 is shown as a single body, the tool may alternatively include separate components such as a cartridge, sonde or skid, and the tool may be combinable with other logging tools.

The logging device includes, for example, a permanent magnet or permanent magnet array 117, which may be made of a samarium-cobalt-magnetic material, and one or more RF antennas 118. The investigation region, or sensitivity zone, represented generally at 127, is a region in the formation in which the static magnetic field is generally uniform, although this is not necessarily required for operation in accordance with the invention. Some embodiments of the invention may take advantage of inherent non-uniformity in the static magnetic field to generate a static magnetic field gradient within the investigation region 127. In other embodiments, pulsed magnetic field gradients may be used to generate or enhance a magnetic field gradient within the investigation region 127. U.S. Pat. No. 5,796,252, for example, which is incorporated herein by reference, describes various embodiments of an antenna that can be incorporated into logging devices of the invention and used to produce pulse field gradients in the investigation region 127. It will be understood that other suitable tool configurations can be utilized for practicing the invention.

While the invention has been described herein with reference to certain examples and embodiments, it will be evident that various modifications and changes may be made to the embodiments described above without departing from the scope and spirit of the invention as set forth in the claims.

What is claimed is:

1. A method of extracting information about a region of fluid-containing earth formation comprising:
   a) applying a magnetic field gradient to said region of earth formation;
   b) applying a first series of oscillating magnetic field pulses to said region of earth formation, said first series of pulses having an initial magnetic field pulse, a first portion followed by a second portion;
   c) detecting magnetic resonance signals generated in (b);
   d) after a wait time, applying a second series of oscillating magnetic field pulses to said region of earth formation, said second series of pulses having an initial magnetic field pulse, a third portion followed by said second portion;
   e) detecting magnetic resonance signals generated in (d); and
   f) analyzing said detected signals to determine the presence of one or more magnetic minerals in said region of earth formation.

2. The method of claim 1, wherein said one or more magnetic minerals are paramagnetic minerals selected from the group consisting of hematite, franklinite, chlorite, glauconite, and siderite or ferromagnetic minerals selected from the group consisting of magnetite and pyrrhortite.

3. The method of claim 1, wherein said magnetic field gradient is a static field gradient.

4. The method of claim 1, wherein said magnetic field gradient is a pulsed field gradient.

5. The method of claim 1, wherein analyzing said detected signals includes separating diffusion and relaxation effects.

6. The method of claim 1 further comprising:
   g) repeating (d) and (e) one or more times, wherein each additional series of pulses, comprises a modified third portion followed by said second portion.

7. The method of claim 6, wherein analyzing the detected signals includes developing a two-dimensional function describing the diffusion and relaxation of said region of earth formation.

8. The method of claim 7, further comprising:
   h) developing a calibration function describing the relationship between diffusion and relaxation representative of at least one of said one or more magnetic minerals;
   i) correlating said calibration function with said two-dimensional function; and
   j) calculating the relative content of at least one of said one or more magnetic minerals in said region of earth formation.

9. The method of claim 1, further comprising determining the relative content of at least one of said one or more magnetic minerals in said region of earth formation.

10. The method of claim 9 wherein analyzing the detected signals includes developing a diffusion distribution of said region of earth formation and a diffusion distribution of said fluid in said region of earth formation.

11. The method of claim 10, wherein determining the relative content of at least one of said one or more magnetic minerals includes determining the percentage of magnetic resonance signals having a diffusion coefficient higher than the diffusion coefficient of said fluid.

12. A logging apparatus comprising:
   a logging tool that is moveable through a borehole; and
   a processor that is coupled with the logging tool, the processor being programmed with instructions which, when executed by the processor:
   cause the logging tool to:
   i) generate a first series of oscillating magnetic field pulses to said region of earth formation, the first series having an initial magnetic field pulse, a first portion followed by a second portion;
   ii) detect magnetic resonance signals produced from the region of earth formation;
   iii) after a wait time, apply a second series of oscillating magnetic field pulses to said region of earth formation, said second series having an initial magnetic field pulse, a third portion followed by said second portion;

iv) detect magnetic resonance signals produced from the region of earth formation; and cause the processor to:

v) analyze the detected magnetic resonance signals to determine the presence of magnetic minerals in the region of investigation.

13. The apparatus of claim 12, wherein (v) includes separating diffusion and relaxation effects.

14. The apparatus of claim 13, wherein (v) includes determining the diffusion coefficient of said region of earth formation.

15. The apparatus of claim 12, wherein the instructions further cause the logging tool to repeat (iii) and (iv) one or more times, wherein each additional series of pulses, comprises an initial magnetic field pulse, a modified third portion followed by said second portion.

16. The apparatus of claim 15, wherein the instructions further cause the processor to develop a two-dimensional function describing the diffusion and relaxation of said region of earth formation.

17. The apparatus of claim 16, wherein the processor is programmed with a calibration function describing the relationship between diffusion and relaxation representative of at least one of said one or more magnetic minerals and wherein the instructions further cause the processor to correlate said calibration function to said two-dimensional function.

18. A method of extracting information about a fluid-containing porous media comprising:

a) applying a magnetic field gradient to said media;

b) applying a first series of oscillating magnetic field pulses to said media, said first series of pulses having an initial magnetic field pulse, a first portion followed by a second portion;

c) detecting magnetic resonance signals generated in (b);

d) after a wait time, applying a second series of oscillating magnetic field pulses to said media, said second series of pulses having an initial magnetic field pulse, a third portion followed by said second portion;

e) detecting magnetic resonance signals generated in (d); and f) analyzing said detected signals to determine the presence of one or more magnetic materials in said media.

19. The method of claim 18, wherein said one or more magnetic materials are magnetic minerals.

20. The method of claim 19, wherein said one or more magnetic minerals are paramagnetic minerals selected from the group consisting of hematite, franklinite, chlorite, glauconite, and siderite or ferromagnetic minerals selected from the group consisting of magnetite and pyrrhortite.

21. The method of claim 18, wherein said magnetic field gradient is a static field gradient.

22. The method of claim 18, wherein said magnetic field gradient is a pulsed field gradient.

23. The method of claim 18, wherein analyzing said detected signals includes separating diffusion and relaxation effects.

24. The method of claim 18 further comprising:

g) repeating (d) and (e) one or more times, wherein each additional series of pulses, comprises an initial magnetic field pulse, a modified third portion followed by said second portion.

25. The method of claim 24, wherein analyzing the detected signals includes developing a two-dimensional function describing the diffusion and relaxation of said media.

26. The method of claim 25, further comprising:

h) developing a calibration function describing the relationship between diffusion and relaxation representative of at least one of said one or more magnetic materials;

i) correlating said calibration function to said two-dimensional function; and j) calculating the relative content of at least one of said one or more magnetic materials in said media.

27. The method of claim 18, further comprising determining the relative content of at least one of said one or more magnetic materials in said media.

28. The method of claim 27 wherein analyzing the detected signals includes developing a diffusion distribution of said media and a diffusion distribution of said fluid in said media.

29. The method of claim 28, wherein determining the relative content of at least one of said one or more magnetic materials includes determining the percentage of magnetic resonance signals having a diffusion coefficient higher than the diffusion coefficient of said fluid.

* * * * *